US00PP09217P

United States Patent [19]

Trees

[11] Patent Number: Plant 9,217

[45] Date of Patent: Jul. 25, 1995

[54] GERANIUM PLANT NAMED 'BFP-721 BRIGHT LILAC'

[75] Inventor: Scott C. Trees, Arroyo Grande, Calif.

[73] Assignee: Geo J. Ball, Inc., West Chicago, Ill.

[21] Appl. No.: 341,991

[22] Filed: Nov. 16, 1994

[51] Int. Cl.[6] ..... A01H 5/00

[52] U.S. Cl. ..... Plt./87.12

[58] Field of Search ..... Plt. 87.12

[56] References Cited

U.S. PATENT DOCUMENTS

P.P. 7,083 12/1989 Hofmann ..... Plt./87.12

P.P. 7,087 12/1989 Hofmann ..... Plt./87.12

*Primary Examiner*—James R. Feyrer

*Attorney, Agent, or Firm*—Burns, Doane, Swecker & Mathis

[57] ABSTRACT

A new and distinct *Pelargonium*×*hortorum* cultivar named BFP-721 Bright Lilac is provided. This new Geranium cultivar was the result of a controlled breeding program wherein the Laura cultivar (U.S. Plant Pat. No. 7,087) was pollinated by the FOX cultivar (U.S. Plant Pat. No. 7,083). The new cultivar forms attractive long-lasting dark lavender semi-double flowers with a white eye. Attractive medium green foliage that lacks zonation is well retained even during shipment. The growth habit is medium self-branching even in the absence of a growth regulator.

1 Drawing Sheet

SUMMARY OF THE INVENTION

The present invention comprises a new and distinct Geranium cultivar, botanically known as *Pelargonium*-×*hortorum* Bailey, and hereinafter is referred to by the cultivar name BFP-721 Bright Lilac.

The new cultivar is the product of a planned breeding program which had as its objective the creation of a new Geranium cultivar that exhibits uniform flowers, medium green foliage, a medium self-branching growth habit that requires no growth regulator, a propensity for rapid rooting, and a stable foliage coloration during shipment.

The breeding program that resulted in the production of the new cultivar of the present invention was carried out in a controlled environment during 1990 at Arroyo Grande, Calif., U.S.A. The female parent (i.e., seed parent) was the Laura cultivar (U.S. Plant Pat. No. 7,087) which exhibits semi-double lavender flowers with medium green foliage. The male parent (i.e., pollen parent) was the Fox cultivar (U.S. Plant Pat. No. 7,083) which exhibits semi-double purple flowers with medium green foliage. The parentage of the new BFP-721 Bright Lilac cultivar can be summarized as follows:

Laura×Fox.

BFP-721 Bright Lilac was discovered and selected during 1990 as a highly distinctive flowering plant among the progeny of the stated cross at Arroyo Grande, Calif., U.S.A. This plant was initially designated BFP-721.

It was found that the new cultivar of the present invention:

(a) exhibits attractive long-lasting dark lavender semi-double florets with a white eye,
(b) forms medium green foliage, and
(c) exhibits a medium self-branching growth habit.

When a plant material of the BFP-721 Bright Lilac cultivar is subjected to standard random amplified polymorphic DNA marker analysis (RAPD) using polymerase chain reaction (PCR) and a known set of DNA primers, it is found to exhibit a distinctive fingerprint map which is on file at the Ball FloraPlant Division of Geo. J. Ball, Inc. at Arroyo Grande, Calif., U.S.A.

The first act of asexual reproduction of the BFP-721 Bright Lilac cultivar was accomplished when vegetative cuttings were taken from the initial selection in a controlled environment at Arroyo Grande, Calif., U.S.A. by a technician working under the direction and supervision of the originator of the new cultivar. Horticultural examination of plants resulting from such asexual propagation during 1992 has demonstrated that the combination of characteristics as herein described for the BFP-721 Bright Lilac cultivar is firmly fixed and is retained through successive generations of such reproduction.

The new BFP-721 Bright Lilac cultivar has not been observed under all possible environmental conditions. Accordingly, the described phenotype may vary somewhat with variations in environment, such as temperature, light intensity, and day length.

Of the many commercial cultivars, the Laura cultivar (U.S. Plant Pat. No. 7,087) is considered to be the most similar. However, when the new cultivar of the present invention is compared to the Laura cultivar, the BFP-721 Bright Lilac cultivar exhibits larger umbels (e.g., approximately 11 to 12 cm.×approximately 8 to 9 cm. vs. approximately 10 to 11 cm.×approximately 5 to 7 cm.). Moreover, each umbel possesses more florets which are slightly smaller than those of the Laura cultivar as specified in greater detail hereafter.

The new cultivar of the present invention is being marketed by Geo J. Ball, Inc. under the Designer trademark.

BRIEF DESCRIPTION OF THE PHOTOGRAPH

The accompanying photograph shows a typical plant of the new BFP-721 Bright Lilac cultivar with colors being as nearly true as it is reasonably possible to make the same in a color illustration of this character. Typical flowers and foliage are depicted. The plant was grown in a greenhouse at West Chicago, Ill., U.S.A.

DETAILED DESCRIPTION

The following observations, measurements and comparisons describe plants grown in Ball FloraPlant's greenhouses located at West Chicago, Ill., U.S.A. under conditions which approximate those generally used in commercial practice. In the following description, color references are made to The R.H.S. Colour Chart of The Royal Horticultural Society, London, England. The color values were determined between 9:00 and 10:00 a.m. on Jul. 21, 1994, under natural light conditions of 2,000 footcandles.

Classification:

*Botanical.*—*Pelargonium* × *hortorum* Bailey, cv. BFP-721 Bright Lilac.

*Commercial.*—Zonal Geranium.

Inflorescence

A. Umbel:

*Average Diameter.*—Approximately 11 to 12 cm. compared to approximately 10 to 11 cm. for the Laura cultivar.

*Average Depth.*—Approximately 8 to 9 cm. compared to approximately 5 to 7 cm. for the Laura cultivar.

*Peduncle Length.*—Approximately 12 to 18 cm. compared to approximately 12 to 20 cm. for the Laura cultivar.

*Pedicel Length.*—Approximately 2.9 to 3.1 cm. compared to approximately 2.9 to 3.5 cm. for the Laura cultivar.

*Number of umbels/plant.*—When grown in a 10 cm. pot at 9 weeks after the sticking of a rooted cutting, there commonly are approximately 5 7 umbels per plant. This compares to approximately 6 to 7 umbels per plant for the Laura cultivar. When plants are grown in the field for 16 weeks, the new cultivar commonly possesses approximately 11 umbels per plant while the Laura cultivar commonly possesses approximately 12 umbels per plant.

Number of florets/umbel.—Plants grown in the greenhouse in 10 cm. pots have approximately 46 to 54 florets per umbel at 9 weeks whereas plants of the Laura cultivar grown in the same manner commonly have approximately 36 to 40 florets per umbel.

Corolla:

*Average Diameter:*—Approximately 4.9 to 5.0 cm. compared to approximately 5.2 to 5.5 cm. for the Laura cultivar.

*Form.*—Both the BFP-721 Bright Lilac cultivar and the Laura cultivar are semi-double and possess approximately 6 to 7 petals per floret.

*Number of Petaloids.*—Both the BFP-721 Bright Lilac cultivar and the Laura cultivar occasionally form 1 to 2 petaloids per floret.

*Color.*—*General tonality from a distance of three meters:* Lilac. Adaxial: Red-purple Group 74B with a white eye on upper two petals. This compares to Red-Purple Group 71D with a white eye on upper two petals for the Laura cultivar. Abaxial: Red-Purple Group 73A with veins of Red-Purple Group 74B. This compares to Red-Purple Group 74C for the Laura cultivar.

C. Bud:

*Shape.*—Oval-rounded.

*Color.*—*Adaxial:* Red-Purple Group 74B. This compares to Red-Purple Group 71D for the Laura cultivar. Abaxial: Red-Purple Group 73A. This compares to Red-Purple Group 74C for the Laura cultivar.

D. Reproductive organs:

*Androecium.*—The anthers are commonly approximately 2 mm. in length. The pollen color is Orange-Red Group 31A for the new cultivar and Orange-Red Group 32A for the Laura cultivar. The filaments are approximately 4 to 7 mm. in length for both the BFP-721 Bright Lilac cultivar and the Laura cultivar.

*Gynoecium.*—The pistil length commonly is approximately 9 mm. There is a single stigma which has a length of approximately 4 mm. which commonly branches into 5 parts, and the style length commonly is approximately 5 mm.

*Fertility.*—Usually does not produce fruits in the absence of mechanical fertilization.

E. Spring Flowering Response Period: Approximately 6 to 7 weeks from rooted cuttings under greenhouse conditions.

F. Outdoor Flowering Production: Freely flowering under outdoor growing conditions with substantially continuous blooming.

G. Durability: Ships well.

Plant

A. Foliage: Dark green with no zone.

*Form.*—Reniform, with a cordate base.

*Margin.*—Crenate.

*Color.*—*Adaxial*: Green Group 137A for both BFP-721 Bright Lilac cultivar and the Laura cultivar. Abaxial: Green Group 137C for both BFP-721 Bright Lilac cultivar and the Laura cultivar.

*Size.*—Approximately 7.7 to 8.6 cm. at widest point and approximately 7.0 to 7.2 cm. at narrowest point. This compares to approximately 7.5 to 8.0 cm. at the widest point and approximately 6.5 to 7.0 cm. at narrowest point for the Laura cultivar.

*Tolerance to botrytis.*—Better than most varieties in this color class.

B. General appearance and form:

*Internode length.*—Commonly varies from approximately 1.0 to 1.5 cm. compared to approximately 1.5 to 2.5 cm. for the Laura cultivar.

*Branching pattern.*—Freely basal branching. No pinching is required to obtain self-branching. A medium self-branching growth habit is observed in the absence of a growth regulator.

*Height.*—Commonly approximately 24 to 29 cm. above a 10 cm. pot at 9 weeks under greenhouse conditions compared to approximately 25 to 30 cm. for the Laura cultivar under the same conditions.

I claim:

1. A new and distinct Geranium plant named BFP-721 Bright Lilac, substantially as herein shown and described, which:

(a) exhibits attractive long-lasting dark lavender semi-double florets with a white eye, (b) forms medium green foliage, and (c) exhibits a medium self-branching growth habit.

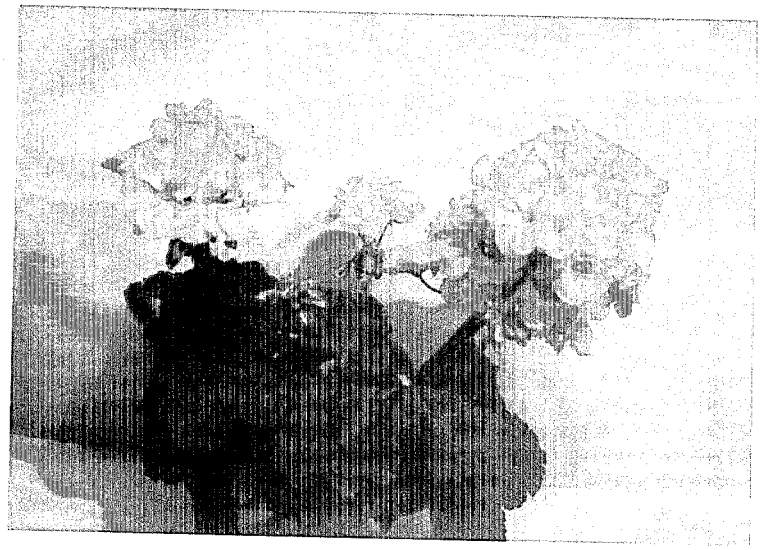

* * * * *